(12) United States Patent
Warren (10) Patent No.: US 6,369,276 B1
(45) Date of Patent: Apr. 9, 2002

(54) CATALYST STRUCTURE FOR KETONE PRODUCTION AND METHOD OF MAKING AND USING THE SAME

(75) Inventor: Jack S. Warren, Blountville, TN (US)

(73) Assignee: EagleView Technologies, Inc., Minneapolis, MN (US)

( * ) Notice: Subject to any disclaimer, the term of this patent is extended or adjusted under 35 U.S.C. 154(b) by 0 days.

(21) Appl. No.: 09/388,504

(22) Filed: Sep. 2, 1999

Related U.S. Application Data (60) Provisional application No. 60/109,261, filed on Nov. 19, 1998, and provisional application No. 60/139,098, filed on Jun. 14, 1999.

(51) Int. Cl.$^7$ ............................................... C07C 45/00
(52) U.S. Cl. ........................ 568/355; 568/338; 568/354
(58) Field of Search ................................ 568/338, 354, 568/355

(56) References Cited

U.S. PATENT DOCUMENTS

| | | |
|---|---|---|
| 3,410,909 A | 11/1968 | Fleischer et al. |
| 3,453,331 A | 7/1969 | Hargis et al. |
| 3,466,334 A | 9/1969 | Young et al. |
| 3,660,491 A | 5/1972 | Thigpen et al. |
| 3,966,822 A | 6/1976 | Fukui et al. |
| 4,060,555 A | 11/1977 | Peterson et al. |
| 4,505,738 A | 3/1985 | Gsell |
| 4,515,626 A | 5/1985 | Szczepanski |
| 4,528,400 A | 7/1985 | Cryberg et al. |
| 4,570,021 A | 2/1986 | Cryberg et al. |
| 4,590,292 A | 5/1986 | Blackwell et al. |
| 4,693,745 A | 9/1987 | Brunner |
| 4,797,152 A | 1/1989 | Brunner |
| 4,803,268 A | 2/1989 | Brunner et al. |
| 4,872,902 A | 10/1989 | Brunner |
| 4,874,899 A | 10/1989 | Hoelderich et al. |
| 4,883,878 A | 11/1989 | Amato et al. |
| 4,964,846 A | 10/1990 | Gais et al. |
| 5,026,916 A | 6/1991 | Tobler |
| 5,124,293 A | 6/1992 | Lindfors et al. |
| 5,366,957 A | 11/1994 | Cain et al. |
| 5,434,152 A | 7/1995 | Huffman et al. |
| 5,453,545 A | 9/1995 | Burello et al. |
| 5,565,399 A | 10/1996 | Fraenkel et al. |
| 5,629,455 A | 5/1997 | Kaufhold et al. |
| 5,656,573 A | 8/1997 | Roberts et al. |
| 5,849,928 A | 12/1998 | Hawkins |
| 6,087,538 A | 7/2000 | Teles et al. |

FOREIGN PATENT DOCUMENTS

| | | |
|---|---|---|
| DE | 36 37 788 A1 | 5/1988 |
| DE | 197 26 666 A1 | 12/1998 |
| EP | 0 085 996 B1 | 8/1983 |
| EP | 0 085 996 A2 | 8/1983 |
| EP | 0 418 175 B1 | 3/1991 |
| EP | 0 507 013 B1 | 10/1992 |
| EP | 0 527 036 B1 | 2/1993 |
| EP | 0 527 037 B1 | 2/1993 |
| EP | 0 560 482 B1 | 9/1993 |
| EP | 0 609 798 A1 | 8/1994 |
| EP | 0 682 659 B1 | 11/1995 |
| GB | 1 435 639 | 5/1976 |
| WO | WO 99/02476 | 1/1999 |
| WO | WO 99/24409 | 5/1999 |

OTHER PUBLICATIONS

G.W. Cannon et al., "Acylation Studies. I Methyl Cyclopropyl Ketone," *Journal of Organic Chemistry*, 17(5):685–692 (May 1952).
International Search Report for PCT/US99/25372 (2 pages).
International Search Report for PCT/US00/24458 (6 pages).
Rhone–Poulenc, Balance (TM) WDG Herbicide, Material Safety Data Sheet prepared Sep. 3, 1998 (7 pages).

*Primary Examiner*—Johann Richter
*Assistant Examiner*—J. Parsa
(74) *Attorney, Agent, or Firm*—Popovich & Wiles, P.A.

(57) ABSTRACT

A catalyst structure and method of making and using the same in a ketone production process. The catalyst structure includes a substantial theoretical monolayer of catalyst on a catalyst support to optimize ketone yield and weight hourly space velocities.

5 Claims, 1 Drawing Sheet

CATALYST STRUCTURE FOR KETONE PRODUCTION AND METHOD OF MAKING AND USING THE SAME

This application claims the benefit of provisional application Ser. No. 60/109,261 filed Nov. 19, 1998 and provisional application Ser. No. 60/139,098 filed Jun. 14, 1999.

BACKGROUND OF THE INVENTION

1. Field of the Invention

The present invention relates generally to chemical reaction catalysts and methods for making and using the same, and more particularly to a catalyst for the production of various organic compounds such as ketones and a method of making the catalyst and using the same in a process of producing the desired ketone. Still more specifically, the present invention relates to use of a theoretical monolayer catalyst to optimize the weight hourly space velocity for a ketone production process in a tube rector.

2. Description of the Prior Art

Numerous literature references cite and disclose various well-known processes for the preparation of ketones. These processes include oxidation of secondary alcohols, Friedel-Crafts acylation, reaction of acid chlorides with organic cadmium compounds, acetoacetic ester synthesis and decarboxylation from acids, among others.

Text and literature references also detail problems associated with these processes to produce ketones. These include problems such as the unavailability and/or cost of raw materials, the requirement of multi-stage processing, the low conversion of raw materials and/or the low selectivity of the desired ketones, and the production of corrosive or hard-to-separate products.

Most ketone manufacturing processes include the reaction of various reactants at specified temperature and pressure ranges in the presence of a catalyst. For example, U.S. Pat. No. 4,528,400 discloses a method of preparing unsymmetrical ketones by a catalytic vapor phase reaction using reactants such as ketones with carboxylic acids in the presence of a ceria-alumina catalyst. U.S. Pat. No. 4,874,899 involves the preparation of unsaturated and saturated ketones in the presence of a catalyst such as a zeolite, a phosphate having a zeolite structure and/or a B, Ce, Fe, Zr or Sr phosphate. U.S. Pat. No. 4,570,021 relates to the preparation of ketones utilizing a ceria-alumina catalyst. U.S. Pat. No. 4,060,555 discloses the production of a class of aliphatic ketones in the presence of Deacon catalysts. U.S. Pat. No. 3,966,822 discloses the preparation of ketones from aldehydes in the presence of zirconium oxide and various other catalysts. U.S. Pat. No. 3,466,334 discloses synthesis of ketones from an aldehyde and an acid in the presence of a catalyst comprised of an alumina-supported oxidized form of lithium. U.S. Pat. No. 3,453,331 discloses a process for the synthesis of ketones from aldehydes using various alumina-supported oxidized forms of various metals. German Patent Application No. P 36 37 788.0 discloses a process for the preparation of a ketone in the presence of catalysts such as ZnO and/or $CeO_2$ doped on aluminum oxide ($Al_2O_3$).

Although a great deal of attention has been given to the selection of feed materials and the process parameters such as temperature and pressure in connection with the production of ketones, little, if any, attention has been given to evaluating the role of the catalyst in the ketone preparation process or to selecting or preparing the catalyst for the purpose of maximizing the conversion and selectivity of the feed material to the desired ketone product. Accordingly, there is a need in the art for a catalyst or catalyst structure useful in the production of ketones which not only allows the reaction to proceed, but which also optimizes the conversion and selectivity of the reaction to the desired ketone and permits conversion and selectivity for various catalyst structures to be reasonably predicted. A need also exists in the art for a method of making such a catalyst and for using such a catalyst in the production of ketones.

SUMMARY OF THE INVENTION

In contrast to the prior art, the present invention relates to a catalyst and catalyst structure for use in the production of organic compounds such as ketones, which has been formulated to optimize the conversion of feed reactants and selectivity to the desired ketone. Further, the present invention relates to a catalyst and catalyst structure, which enables a dramatic increase in weight hourly space velocity (WHSV) of the production reaction without significantly adversely affecting the conversion and selectivity of the reaction. Still further, a method has been developed in accordance with the present invention for making the above-mentioned catalyst and for using such catalyst in the production of the desired ketone.

More specifically, the catalyst of the present invention comprises a catalyst support having an available or effective surface area of at least about 20 $m^2$ per gram of support or about 20 to 500 $m^2$ per gram of support. As used herein the terms "available" surface area or "effective" surface area of a catalyst support is the surface area of a catalyst support that is available to receive at least a monolayer of a selected catalyst. The catalyst structure of the present invention also includes a theoretical monolayer or substantial theoretical monolayer of catalyst applied to the available or effective surface area of the catalyst support. As used herein, the term "theoretical monolayer" means a film layer one molecule thick of a catalyst on the effective surface area of a catalyst support. The present invention recognizes that for reactions involved in the preparation of various organic compounds such as ketones, catalyst supports whose effective surface area is provided with more or less than a theoretical monolayer of the catalyst results in conversion and selectivity values, which are less than optimal.

The present invention also relates to a method of making the above-described catalyst and using the same in the production of ketones. More specifically, the method of making the catalyst involves the steps of providing a catalyst support having an effective surface area of at least 20 $m^2$ or about 20 to 500 $m^2$ per gram of catalyst support and then applying a theoretical monolayer of catalyst to the effective surface area of the catalyst support. The method of using the catalyst includes combining the feed streams of the desired organic compound or ketone producing reaction in the presence of heat, pressure and the catalyst in a reaction vessel, maintaining the feed stream at a rate sufficient for the desired reaction to occur and then separating the desired ketone from the exit stream. With a theoretical monolayer of catalyst, it has been found that the weight hourly space velocity (WHSV) of the reaction can be significantly increased and conversion and selectivity of the desired ketone can be optimized.

Accordingly, it is an object of the present invention to provide an improved catalyst structure for use in the production of organic compounds such as ketones.

Another object of the present invention is to provide a catalyst structure usable in a ketone production process, which optimizes the conversion and selectivity relative to the desired ketone.

Another object of the present invention is to provide a catalyst structure for a ketone production process by which the conversion and selectivity of the desired ketone can be predicted.

A further object of the present invention is to provide a catalyst structure for a ketone production process in which the weight hourly space velocity can be significantly increased.

A still further object of the present invention is to provide a method of making the catalyst structure described above.

A still farther object of the present invention is to provide a method for using the above-described catalyst structure in the production of a desired ketone.

These and other objects of the present invention will become apparent with reference to the drawing, the description of the preferred embodiment and the appended claims.

DESCRIPTION OF THE PREFERRED EMBODIMENT

The present invention relates generally to a catalyst or catalyst structure for use in the production of various organic compounds such as ketones. Although the concepts of the present invention are applicable to ketones generally, the catalyst structure described in the preferred embodiment and method has particular applicability to the production of methyl cyclopropyl ketone (MCPK). Accordingly, the description of the preferred embodiment and method of the present invention will be described with respect to catalysts or catalyst structures useful in the production of MCPK.

The catalyst structures useful in the present invention are comprised of a catalyst support having an effective surface area and a catalyst applied to such effective surface area. Numerous companies offer products that can be used to support a catalyst for chemical synthesis. Engelhard and Condea are examples of such companies. With current manufacturing technology, these companies offer catalyst support materials of various chemical composition, porosity, density, effective surface area, shape, size and cross section. Examples of catalyst supports include metals or metal oxides such as alumina, silica, titania, zirconia and mixtures thereof and naturally occurring clay material such as montmorillonite or kaolin. These existing catalyst support materials generally have effective surface areas ranging from about 20 to 500m$^2$ per gram. Preferred substrates for use in the present invention include substrates such as aluminum oxide ($Al_2O_3$), zinc oxide (ZnO), zirconium oxide ($ZrO_2$), titanium oxide ($TiO_2$) or combinations of these oxides.

To prepare the catalyst structure in accordance with the present invention, a catalyst useful in the production of ketones is applied to the surface area of the catalyst support. This may be done by any method common in the art. In one embodiment in which cerium oxide ($CeO_2$) is applied to a porous aluminum oxide ($Al_2O_3$) cylindrical support, such $CeO_2$ catalyst structure is prepared by impregnating the $Al_2O_3$ cylindrical structure with a solution of a predetermined concentration of cerium acetate hydrate $Ce(O_2CCH_3)_3 \cdot 1.5H_2O$ using the incipient wetness method (dropwise), at ambient temperature. This gives 1.0. gram of $CeO_2/2.0$ grams of this precursor. Following such impregnation, the catalyst support is dried at 450° C. for 12 hours. The hydrate is dissolved as 200 grams per liter of aqueous solution. Odd percentages can be obtained by using 10 milliliters of the solution for each one (1) gram of actual catalyst needed. For ~5 wt % $CeO_2$ catalyst, 50 milliliters of this saturated solution is used per 100 grams of catalyst support. For impregnation of catalyst on the catalyst support greater than 5%, multiple applications are used, with an intermediate drying step of 120° C., to insure uniform coverage. For ~10 wt % $CeO_2$ catalyst, two (2) 50 milliliter solutions are used. The resulting catalyst support with impregnated catalyst is then oven-dried at 450° C. for twelve (12) hours, prior to pretreatment in the reactor. For all percentages, lesser quantities of the solution can be used. Other precursors, such as cerium nitrate and techniques, such as spray or tumble-drying, known to those skilled in the art, can be used to apply the catalyst.

A variety of catalysts are commonly applied to catalyst supports for use in the production of organic compounds and specifically in the production of ketones such as MCPK. These catalysts include, but are not limited to, metal or metal oxides such as the oxides of Cerium ($CeO_2$ or $CeO_3$), zirconium ($ZrO_2$), Zinc (ZnO), or other lanthanides, group IIIB, IVB and VB metals or metal oxides. Conventionally, standard weight percentages of catalyst per unit weight of the support are prepared. For example, a 5% catalyst comprises 0.05 grams of catalyst per gram of catalyst support. Catalysts of 5%, 10% and other multiples of 5% are commonly prepared. This is accomplished by techniques known to those skilled in the art.

A problem with this approach, however, is that many, if not all, of the catalyst supports useful in organic compound production generally, and ketone production specifically, function negatively relative to the preferred reaction. This is because such catalyst supports retard the desired reaction or do not promote or assist the desired reaction as much as the catalyst itself, either with respect to conversion or selectivity, or both. Thus, if the amount of catalyst applied to the catalyst support is not sufficient to cover the effective surface area of the catalyst support, a portion of the effective surface area of the catalyst support remains uncoated and is thus free to contact the feed reactants as they pass through the reaction chamber. Because of these exposed catalyst support surface areas, the reaction (either conversion, selectivity, or both) is negatively affected.

On the other hand, if excess catalyst is applied to the effective surface area of the catalyst support, the excess catalyst tends to fill or plug some of the pores within the catalyst support, thereby resulting in a decrease of the effective surface area of the catalyst support, and thus a decrease in the catalyst exposed to the reaction materials as they pass through the catalytic bed.

Accordingly, the concept of the present invention is to provide the effective surface area of a catalyst support with substantially a theoretical monolayer of the desired catalyst. For purposes of the present invention, the term theoretical monolayer (TML) is a thin film or layer of a material (catalyst) applied to a surface at a thickness of one molecule. Thus, a theoretical monolayer catalyst in accordance with the present invention is a catalyst structure in which a desired catalyst is applied to the effective surface area of a catalyst support at a thickness of one molecule of the catalyst. When applied, the catalyst or catalyst structure is expressed as weight percent of catalyst per unit weight of catalyst support. By applying a theoretical monolayer of catalyst to the effective surface area of a catalyst support, catalysis conditions are optimized. Specifically, an optimal quantity of catalyst is available to facilitate the desired reaction. Thus, the negative effects of the exposed catalyst support are eliminated in the case where there is too little catalyst and the negative effects of filling pores and losing effective surface area are eliminated in the case where there is too much catalyst. Accordingly, the catalyst structure in accordance with the present invention includes a catalyst support with an effective surface area and a substantially theoretical monolayer of catalyst applied to such effective surface area. As used herein, a substantially theoretical monolayer shall mean plus or minus 10% of a theoretical monolayer.

Although conventional catalyst supports useful for the production of organic compounds generally and ketones specifically having effective surface areas ranging from about 20 to 500 m² per gram of support, the preferred catalyst support material for use in the production of ketones in accordance with the present invention has an effective surface area of about 20–500 m² per gram of support, more preferably about 20–200 m² per gram and most preferably about 30–180 m per gram of support.

By providing a substantially theoretical monolayer of catalyst to the catalyst support to optimize the catalyst structure, it has been found that the weight hour space velocity (WHSV) of organic compound production reactions requiring catalysts can be significantly increased without significantly adversely affecting the conversion or selectivity of the desired reaction. Specifically, a substantial theoretical monolayer catalyst in accordance with the present invention facilitates a WHSV of greater than 2, more preferably greater than 5, and most preferably greater than 10.

A first step in making the catalyst structure of the present invention is to determine or calculate the amount of catalyst needed to provide a theoretical monolayer of that catalyst to a particular catalyst support. By knowing the effective surface area of a catalyst support and by knowing the crystallographic data for the catalyst, the theoretical monolayer for that catalyst can be calculated.

The effective surface area of commercially available catalyst supports are commonly provided by the supplier of the support material or can be measured using various commercially available instruments. There are numerous types of commercial instruments used to determine surface areas by adsorption of liquid nitrogen (the "BET" method). One of these instruments calculates the surface area based on a full adsorption/desorption Volume of $N_2$ vs. Pressure curve at a range of pressures between roughly $10^{-3}$ torr and 760 torr. This method gives very accurate numbers, but is time consuming. Newer instruments are fully automated and have liquid nitrogen flow controllers. A second estimates the surface area from the BET equation and adsorption/desorption at only a single pressure and is a much quicker method. The surface areas obtained seldom differ from more accurate numbers by more than 10%. Effective surface area of a catalyst support is commonly expressed in the form or surface area or square units per weight of the catalyst support. Typical effective surface area information is expressed in square meters per gram or m²/g.

Crystallographic data is also available for catalysts and is available from various sources such as the *CRC Handbook of Chemistry and Physics,* 54th edition, 1972, among others. From the crystal structure of the relevant oxide, one can estimate which crystal planes will most likely be exposed. Thus, one can find the dimensions of the unit cell (the repeat unit). Using geometry, the number of atoms in the unit cell exposed on that plane, and therefore the surface area occupied by a single molecule in that plane can be calculated. By knowing or determining the surface area which one molecule of the catalyst will occupy when applied to a catalyst support, and by knowing the molecular weight of the catalyst, the grams of catalyst needed to cover a particular surface area one molecule thick can be calculated. By combining the information regarding the effective surface area of a catalyst support expressed in m² per gram and the information regarding the grams of catalyst necessary to cover a square meter of surface area, the weight percent of the catalyst relative to the catalyst support can be calculated.

The following illustrate calculations to determine the theoretical monolayer for a catalyst structure in which cerium oxide ($CeO_2$) is the catalyst and aluminum oxide ($Al_2O_3$) is the catalyst support for a catalyst structure in which cerium oxide ($CeO_2$) is the catalyst and zirconium oxide ($ZrO_2$) is the catalyst support and for a catalyst structure in which zinc oxide ($ZnO$) is the catalyst and aluminum oxide ($Al_2O_3$) is the catalyst support.

$$CeO_2/Al_2O_3$$

Theoretical Monolayer Catalyst

In this calculation, the effective surface area of the porous $Al_2O_3$ catalyst support, which is provided by the manufacturers of such material, is about 178 m²/g.

From the *CRC Handbook of Chemistry and Physics,* 54th edition, 1972, the crystallographic data for cerium oxide (cerianite) is as follows:

| Crystallographic Data for Cerianite ($CeO_2$) | |
|---|---|
| Crystal System | Cubic |
| Space Group | Fm3m (225) |
| Structure Type | Fluorite |
| Z | 4 |
| Å | 5.4100 (±.0020) |
| Cell Volume | 159.43 × $10^{-24}$ (±.180) |
| Molar Volume | 28.853 cm3 (±.026) |
| X-Ray Density | 7.216 |

From the above information and data, the amount of the $CeO_2$ catalyst needed to provide a theoretical monolayer on the $Al_2O_3$ catalyst support can be calculated as follows:

Ionic Radius: $Ce^{3+}$=1.14 Å; $Ce^{4+}$=0.97 Å; angstrom (Å)=1×$10^{-10}$ meter From "X-Ray Crystallographic Data of Minerals, CRC Handbook of Chemistry and Physics", $CeO_2$ has a Cubic Crystal System and a Fluorite Structure Type.

| (100) Plane: | 5.41 × 5.41 | 1 Atoms/Unit Cell |
|---|---|---|
| (111) Plane: | 5.41 × 7.65 | 1.5 Atoms/Unit Cell |

1 Molecule $CeO_2$ = 0.2927 nm²    (100) Plane
1 Molecule $CeO_2$ = 0.2759 nm²    (111) Plane
AVG. ~0.284 nm²/Molecule    [50% (100); 50% (111)]

-continued $$\text{Factor} = \frac{[1 \text{ Molecule}]}{0.284 \text{ nm}^2} \frac{(10^9 \text{ nm})^2}{M^2} \frac{(\text{Mol})}{602 \times 10^{23} \text{ Molecule}} \frac{(172.1 G)}{\text{Mol}}$$

Factor = 1.01 × 10$^{-3}$ G CeO$_2$/M$^2$

| Catalyst Support (Al$_2$O$_3$) Surface Area | Theoretical Monolayer |
|---|---|
| Condea = 182 M$^2$/G → | 0.184 G CeO$_2$/G Al$_2$O$_3$ |
| Titania = 164 M$^2$/G → | 0.166 G CeO$_2$/G Al$_2$O$_3$ |
| Engelhard = 189 M$^2$/G → | 0.191 G CeO$_2$/G Al$_2$O$_3$ |
| Average = 178 M$^2$/G → | 0.180 G CeO$_2$/G Al$_2$O$_3$ |
| | (~18% CeO$_2$/Al$_2$O$_3$) |

Accordingly, via the above calculation, it can be determined that a catalyst structure having approximately 18 weight percent (18%) of the catalyst (0.18 grams of CeO$_2$/gram of Al$_2$O$_3$) results in a theoretical monolayer catalyst structure.

CeO$_2$/SrO$_2$

Theoretical Monolayer Catalyst

In this calculation, the effective surface area of the porous ZrO$_2$ catalyst support, which is provided by the manufacturer (Engelhard) is about 33 m$^2$/g.

As in the example above, the amount of CeO$_2$ catalyst needed to provide a theoretical monolayer on the ZrO$_2$ catalyst support can be calculated as follows:

Ionic Radius: Ce$^{3+}$=1.14 Å; Ce$^{4+}$=0.97 Å; angstrom (Å)=1×10$^{-10}$ meter From "X-Ray Crystallographic Data of Minerals, CRC Handbook of Chemistry and Physics", CeO$_2$ has a Cubic Crystal System and a Fluorite Structure Type.

(100) Plane:  5.41 / 5.41   1 Atoms/Unit Cell (111) Plane: 5.41 / 7.65   1.5 Atoms/Unit Cell

| 1 Molecule CeO$_2$ = 0.2927 nm$^2$ | (100) Plane |
| 1 Molecule CeO$_2$ = 0.2759 nm$^2$ | (111) Plane |
| AVG. ~0.284 nm$^2$/Molecule | [50% (100); 50% (111)] |

$$\text{Factor} = \frac{[1 \text{ Molecule}]}{0.284 \text{ nm}^2} \frac{(10^9 \text{ nm})^2}{M^2} \frac{(\text{Mol})}{602 \times 10^{23} \text{ Molecule}} \frac{(172.1 G)}{\text{Mol}}$$

Factor = 1.01 × 10$^{-3}$ G CeO$_2$/M$^2$

| Catalyst Support (ZrO$_2$) Surface Area | Theoretical Monolayer |
|---|---|
| Engelhard = 33 M$^2$/G → | 0.033 G CeO$_2$/G ZrO$_2$ |
| | (~3% CeO$_2$/ZrO$_2$) |

Accordingly, via the above calculation, it can be determined that a catalyst structure having approximately three weight percent (3%) of the catalyst (0.03 grams of CeO$_2$/gram of ZrO$_2$) results in a theoretical monolayer catalyst structure.

ZnO/Al$_2$O$_3$

Theoretical Monolayer Catalyst

In the same manner, the TML for a catalyst structure in which ZnO is the catalyst and Al$_2$O$_3$ is the catalyst support can be calculated. In this calculation, the effective surface area of the porous Al$_2$O$_3$ catalyst support, which is provided by the manufacturers of such material, is about 178 m$^2$/g.

From the *CRC Handbook of Chemistry and Physics*, 54th edition, 1972, the crystallographic data for zincite (ZnO) is as follows:

| Crystallographic Data for Zincite (ZnO) | |
|---|---|
| Crystal System | Hexagonal |
| Space Group | P63mc (186) |
| Structure Type | Zincite |
| Z | 2 |
| Å | 3.2495 (±.0005) |
| Cell Volume | 47.615 × 10$^{-24}$ (±.015) |
| Molar Volume | 14.338 cm3 (±.005) |
| X-Ray Density | 5.6750 (±.0018) |

From the above information and data, the amount of the ZnO catalyst needed to provide a theoretical monolayer on the Al$_2$O$_3$ catalyst support can be calculated as follows:

Ionic Radius: Zn$^{2+}$=0.60 Å; angstrom (Å)=1×10$^{-10}$ meter

From "X-Ray Crystallographic Data of Minerals, CRC Handbook of Chemistry and Physics", ZnO has a Hexagonal Crystal System and a Zincite Structure Type.

(100) Plane:  3.25 / 3.25 / 3.25   1 Atoms/Unit Cell

1 Molecular ZnO = 0.2020 nm$^2$   (100) Plane $$\text{Factor} = \frac{[1 \text{ Molecule}]}{0.2020 \text{ nm}^2} \frac{(10^9 \text{ nm})^2}{M^2} \frac{(\text{Mol})}{602 \times 10^{23} \text{ Molecule}} \frac{(81.39 G)}{\text{Mol}}$$

Factor = .6693 × 10$^{-3}$ G ZnO/M$^2$

| Catalyst Support (1.5 mm Cylinders-Al$_2$O$_3$) Surface Area | Theoritical Monolayer |
|---|---|
| Condea = 182 M$^2$/G → | 0.1218 G ZnO/G Al$_2$O$_3$ |
| Titania = 164 M$^2$/G → | 0.1098 G ZnO/G Al$_2$O$_3$ |
| Engelhard = 189 M$^2$/G → | 0.1265 G ZnO/G Al$_2$O$_3$ |
| Average = 178 M$^2$/G → | 0.1193 G ZnO/G Al$_2$O$_3$ |
| | (~12% ZnO/Al$_2$O$_3$) |

Accordingly, via the above calculation, it can be determined that a catalyst structure having approximately 12 weight percent (12%) of the catalyst (0.12 grams of ZnO/gram of Al$_2$O$_3$) results in a theoretical monolayer catalyst structure.

EXAMPLE 1

In the following example, the TML for CeO$_2$ catalyst on an Al$_2$O$_3$ catalyst support was calculated as described above. In this calculation, 178 m$^2$/g was used as the effective surface area of the Al$_2$O$_3$. As shown in Table 1, this is the average of three suppliers. The TML of CeO$_2$ was also calculated for each of these three effective area values. The results are shown in Table 1. Table 1 also shows the percentage of effective surface area of Al$_2$O$_3$ catalyst support covered for catalyst structures of 5%, 10%, 15%, 20% and a TML. Table 2 shows the percentage of effective area of Al$_2$O$_3$ catalyst support not covered for the above catalysts.

Next, catalyst structures for 5%, 10%, 15%, 20% and a TML were prepared. In preparing the TML catalyst, 178 was used as the effective surface area of the $Al_2O_3$ support, thereby resulting in a TML percentage of about 18%. The procedure for preparing these catalyst structures is as follows:

The $CeO_2$ catalyst is prepared by impregnating the porous, catalyst support with cerium acetate hydrate (Aldrich), $Ce(O_2CCH_3)_3 \cdot 1.5H_2O$, which gives 1.0 g $CeO_2$/2.0 g of the hydrate. The hydrate is dissolved as 200 g/L aqueous, saturated solution. The catalyst support is dried at 450° C. for twelve (12) hours. Impregnation is by the incipient wetness method (drop-wise), at ambient temperature. The aqueous solution can be divided to obtain the actual amount of catalyst necessary for the impregnation. Odd percentages can be obtained by using 10 milliliters of the solution for each one (1) gram of actual catalyst needed. Accordingly, for ~5 wt % $CeO_2$ catalyst, 50 milliliters of this saturated solution is used per 100 grams of catalyst support, for ~10% $CeO_2$ catalyst, two (2) 50 ml solutions are used, for ~15% $CeO_2$ catalyst, three (3) 50 ml solutions are used and for ~20% $CeO_2$ catalyst, four (4) 50mi solutions are used. For an 18% theoretical monolayer catalyst, three 50 ml solutions and one 30 ml solution are used. For multiple applications as described above, an intermediate drying step at 120° C. is utilized between each application.

The data from Table 3 indicates that the $Al_2O_3$ catalyst support, with its 100% surface area exposed, in combination with the high temperature and pressure in the tube reactor, acts as a catalyst for the conversion reaction of RIM; however, selectivity to the desired product (MCPK) is quite limited. Even with very low cost raw materials ($R_1M$), a process using the $Al_2O_3$ support alone to produce MCPK would not be acceptable.

Choosing a catalyst that offers a high conversion of a raw material and selectivity to a desired product is a very important step in chemical process development. The data in Tables 4–8 indicates that $CeO_2/Al_2O_3$ is a good choice as a catalyst and, in general, offers a viable process. The data in the tables shows that the 15% catalyst and the theoretical monolayer catalyst (TML), both, maintain high conversion and selectivity with a significant increase in WHSV over the 5% and 10% catalyst. The data in the tables also shows that the 20% catalyst data offers no real advantage over the 15% or TML catalyst. This is believed to result from the fact that catalyst loading greater than the theoretical monolayer usually results in multiple catalyst layers, which fill some of the surface pores of the catalyst support and thus cause an actual reduction in the total effective surface area of the support.

TABLE 1

| | Surface Area $M^2/G$ | Theoretical Monolayer G $CeO_2$/G $Al_2O_3$ | $CeO_2$/G $Al_2O_3$ | | | | |
|---|---|---|---|---|---|---|---|
| | | | 5% | 10% | 15% | TML | 20% |
| | | | Surface Area of ($Al_2O_3$) Catalyst Support Covered | | | | |
| Condea | 182 | 0.184 | 27.2% | 54.3% | 81.5% | 100.0% | 108.0% |
| Titania | 164 | 0.166 | 30.1% | 60.2% | 90.4% | 100.0% | 120.0% |
| Engelhard | 189 | 0.191 | 26.2% | 52.4% | 78.5% | 100.0% | 105.0% |
| Average | 178 | 0.180 | 27.8% | 55.6% | 83.3% | 100.0% | 111.0% |

TABLE 2

| | Surface Area $M^2/G$ | Theoretical Monolayer G $CeO_2$/G $Al_2O_3$ | $CeO_2$/G $Al_2O_3$ | | | | |
|---|---|---|---|---|---|---|---|
| | | | 5% | 10% | 15% | TML | 20% |
| | | | Surface Area of ($Al_2O_3$) Catalyst Support Not Covered | | | | |
| Condea | 182 | 0.184 | 72.8% | 45.7% | 18.5% | 0.0% | −8.0% |
| Titania | 164 | 0.166 | 69.9% | 39.8% | 9.6% | 0.0% | −20.0% |
| Engelhard | 189 | 0.191 | 73.8% | 47.6% | 21.5% | 0.0% | 5.0% |
| Average | 178 | 0.180 | 72.2% | 44.4% | 16.7% | 0.0% | −11.0% |

Each of these catalyst structures was then used as the catalyst in a methyl cyclopropyl ketone (MCPK) test production process using acetic acid ($R_2M$) and cyclopropanecarboxylic acid (($R_1M$) as the feed reactants in a ratio of 4:1 ($R_2M:R_1M$). The above processes were conducted at temperatures of 410–450° C., at a pressure of about 30 psig and in a ½ inch I.D. stainless steel catalytic tube reactor with a catalytic bed filled with glass beads, catalyst, glass beads (of approximately ⅓, ⅓, ⅓). An internal thermocouple was located at the catalytic bed for monitoring the temperature. Pressure was controlled using a diaphragm-type backpressure regulator. Table 3 shows the conversion and selectivity data for various WHSV using only the $Al_2O_3$ catalyst support. Tables 4, 5, 6 and 8 show conversion and selectivity data for 5%, 10%, 15% and 20% catalyst systems, respectively, while Table 7 shows conversion and selectivity data for a theoretical monolayer of $CeO_2$ catalyst of about 18% $CeO_2/Al_2O_3$.

TABLE 3

| | $Al_2O_3$ | |
|---|---|---|
| | Conversion | Selectivity |
| | $R_1M$ | $USK_1$ |
| WHSV | % | % |
| 1 | 93 | 40 |
| 2 | 84 | 41 |
| 3 | 82 | 28 |
| 4 | 71 | 30 |
| 7 | 60 | 28 |

TABLE 4

5% $CeO_2/Al_2O_3$

| WHSV | Conversion $R_1M$ % | Selectivity $USK_1$ % |
|---|---|---|
| 2 | 98 | 64 |
| 3 | 91 | 62 |
| 4 | 82 | 75 |
| 5 | 70 | 52 |
| 6 | 77 | 31 |

TABLE 5

10% $CeO_2/Al_2O_3$

| WHSV | Conversion $R_1M$ % | Selectivity $USK_1$ % |
|---|---|---|
| 2 | 99 | 67 |
| 3 | 98 | 70 |
| 4 | 98 | 64 |
| 5 | 91 | 62 |
| 6 | 90 | 60 |

TABLE 6

15% $CeO_2/Al_2O_3$

| WHSV | Conversion $R_1M$ % | Selectivity $USK_1$ % |
|---|---|---|
| 4 | 99 | 65 |
| 6 | 96 | 72 |
| 8 | 99 | 71 |
| 10 | 97 | 72 |
| 12 | 96 | 72 |
| 14 | 95 | 70 |
| 16 | 95 | 68 |

TABLE 7

~18% (TML) $CeO_2/Al_2O_3$

| WHSV | Conversion $R_1M$ % | Selectivity $USK_1$ % |
|---|---|---|
| 4 | 98 | 72 |
| 6 | 99 | 70 |
| 8 | 99 | 71 |
| 10 | 97 | 72 |
| 12 | 96 | 72 |
| 14 | 95 | 70 |

TABLE 8

20% $CeO_2/Al_2O_3$

| WHSV | Conversion $R_1M$ % | Selectivity $USK_1$ % |
|---|---|---|
| 2 | 93 | 68 |
| 6 | 97 | 62 |
| 8 | 86 | 76 |

TABLE 8-continued

20% $CeO_2/Al_2O_3$

| WHSV | Conversion $R_1M$ % | Selectivity $USK_1$ % |
|---|---|---|
| 14 | 61 | 70 |
| 16 | 56 | 64 |

EXAMPLE 2

In the following example, the TML for $CeO_2$ catalyst on a $ZrO_2$ catalyst support was calculated as described above. In this calculation, 34 $m^2/g$ was used as the effective surface area of the $ZrO_2$. As shown in Table 9, this is the average of three samples. The TML of $CeO_2$ was also calculated for each of these three effective area values. The results are shown in Table 9. Table 9 also shows the percentage of effective surface area of $ZrO_2$ catalyst support covered for catalyst structures of 2%, 3%, 4% and a TML. Table 10 shows the percentage of effective area of $ZrO_2$ catalyst support not covered for the above catalysts.

Next, catalyst structures for 2%, 3%, 4% and a TML were prepared. In preparing the TML catalyst, 34 $M^2G$ was used as the effective surface area of the $ZrO_2$ support, thereby resulting in a TML percentage of about 3.4% The procedure for preparing these catalyst structures was similar to that described in Example 1 above.

Each of these catalyst structures was then used as the catalyst in a methyl cyclopropyl ketone (MCPK) test production process using acetic acid ($R_2M$) and cyclopropanecarboxylic acid (($R_1M$) as the feed reactants in a ratio of 4:1 ($R_2M:R_1M$). The above processes were conducted at the same temperatures and pressures and using similar equipment as that described in Example 1. Table 11 shows the conversion and selectivity data for various WHSV using only the $ZrO_2$ catalyst support. Tables 12, 13 and 15 show conversion and selectivity data for 2%, 3% and 4% catalyst systems, respectively, while Table 14 shows conversion and selectivity data for a theoretical monolayer of $CeO_2$ catalyst of about 3.4% $CeO_2/ZrO_2$.

The data from Table 11 indicates that the ZrO2 catalyst support, with its 100% surface area exposed, in combination with the high temperature and pressure in the tube reactor, acts as a catalyst for the conversion reaction of RIM; however, selectivity to the desired product (MCPK) is quite limited. Even with very low cost raw materials ($R_1M$), a process using the $ZrO_2$ support alone to produce MCPK would not be acceptable.

The data in Tables 12–15 indicates that $CeO_2/ZrO_2$ is a good choice as a catalyst and, in general, offers a viable process. The data in table 14 shows that the theoretical monolayer catalyst (TML) maintains high conversion and selectivity with a significant increase in WHSV over the other catalyst structures. The data in the tables also shows that the 4% catalyst data offers no real advantage, and in fact distinct disadvantages, over the TML catalyst. This is believed to result from the fact that catalyst loading greater than the theoretical monolayer usually results in multiple catalyst layers, which fill some of the surface pores of the catalyst support and thus cause an actual reduction in the total effective surface area of the support.

TABLE 9

| | Surface Area M²/G | Theoretical Monolayer G CeO₂/G ZrO₂ | CeO₂/G ZrO₂ | | | | |
|---|---|---|---|---|---|---|---|
| | | | 1% | 2% | 3% | TML | 4% |
| | | | Surface Area of (ZrO₂) Catalyst Support Covered | | | | |
| Engelhard | 28 | 0.0283 | 35.3% | 70.7% | 106.0% | 100.0% | 141.3% |
| Engelhard | 35 | 0.0354 | 28.2% | 56.5% | 84.7% | 100.0% | 112.9% |
| Engelhard | 39 | 0.0394 | 25.4% | 50.8% | 76.1% | 100.0% | 101.5% |
| Average | 34 | 0.0343 | 29.2% | 58.3% | 87.5% | 100.0% | 116.6% |

TABLE 10

| | Surface Area M²/G | Theoretical Monolayer G CeO₂/G ZrO₂ | CeO₂/G ZrO₂ | | | | |
|---|---|---|---|---|---|---|---|
| | | | 1% | 2% | 3% | TML | 4% |
| | | | Surface Area of (ZrO₂) Catalyst Support Covered | | | | |
| Engelhard | 28 | 0.0283 | 64.7% | 29.3% | −6.0% | 0.0% | −41.3% |
| Engelhard | 35 | 0.0354 | 71.8% | 43.5% | 15.3% | 0.0% | −12.9% |
| Engelhard | 39 | 0.0394 | 74.6% | 49.2% | 23.9% | 0.0% | −1.5% |
| Average | 34 | 0.0343 | 70.8% | 41.7% | 12.5% | 0.0% | −16.6% |

TABLE 11

ZrO₂

| WHSV | Conversion R₁M % | Selectivity USK₁ % |
|---|---|---|
| 2 | 95 | 42 |
| 4 | 92 | 40 |
| 6 | 89 | 35 |
| 8 | 89 | 33 |
| 10 | 88 | 32 |
| 12 | 88 | 31 |
| 14 | 87 | 29 |

TABLE 12

2% CeO₂/ZrO₂

| WHSV | Conversion R₁M % | Selectivity USK₁ % |
|---|---|---|
| 2 | 78 | 60 |
| 4 | 87 | 74 |
| 6 | 85 | 72 |
| 8 | 82 | 65 |
| 10 | 75 | 55 |

TABLE 13

3% CeO₂/ZrO₂

| WHSV | Conversion R₁M % | Selectivity USK₁ % |
|---|---|---|
| 2 | 86 | 82 |
| 4 | 90 | 83 |
| 6 | 91 | 85 |
| 8 | 91 | 86 |
| 10 | 92 | 83 |

TABLE 14

~3.4% (TML) CeO₂/ZrO₂

| WHSV | Conversion R₁M % | Selectivity USK₁ % |
|---|---|---|
| 2 | 86 | 83 |
| 4 | 90 | 85 |
| 6 | 93 | 85 |
| 8 | 95 | 86 |
| 10 | 96 | 87 |
| 12 | 97 | 84 |
| 14 | 94 | 82 |

TABLE 15

4% CeO₂/ZrO₂

| WHSV | Conversion R₁M % | Selectivity USK₁ % |
|---|---|---|
| 2 | 78 | 55 |
| 4 | 82 | 62 |
| 6 | 84 | 63 |
| 8 | 86 | 68 |
| 10 | 80 | 62 |

The operating conditions for both Examples 1 and 2 are set forth in the table below:

| | Operating Conditions | |
|---|---|---|
| Table | Property | Control |
| 3-15 | R₁M | Cyclopropanecarboxylic Acid |
| 3-15 | R₂M | Acetic Acid |
| 3-15 | USK₁ | Methyl Cyclopropyl Ketone |
| 4-8 | Catalyst | CeO₂/Al₂O₃ |
| 3 | Catalyst | Al₂O₃ Catalyst Support Only |

-continued

Operating Conditions

| Table | Property | Control |
|---|---|---|
| 3-15 | Ratio $R_2M:R_1M$ | 4:1 |
| 3-15 | Temperature | 410–450° C. |
| 3-15 | Pressure | ~30 PSIG |
| 3-7 | Surface Area | ~78 $M^2/G$ |
| 8 | Surface Area | ~152 $M^2/G$ |
| 11 | Catalyst | $ZrO_2$ Catalyst Support Only |
| 11-15 | Surface Area | ~34 $M^2/G$ |
| 12-15 | Catalyst | $CeO_2/ZrO_2$ |

Figure 1:
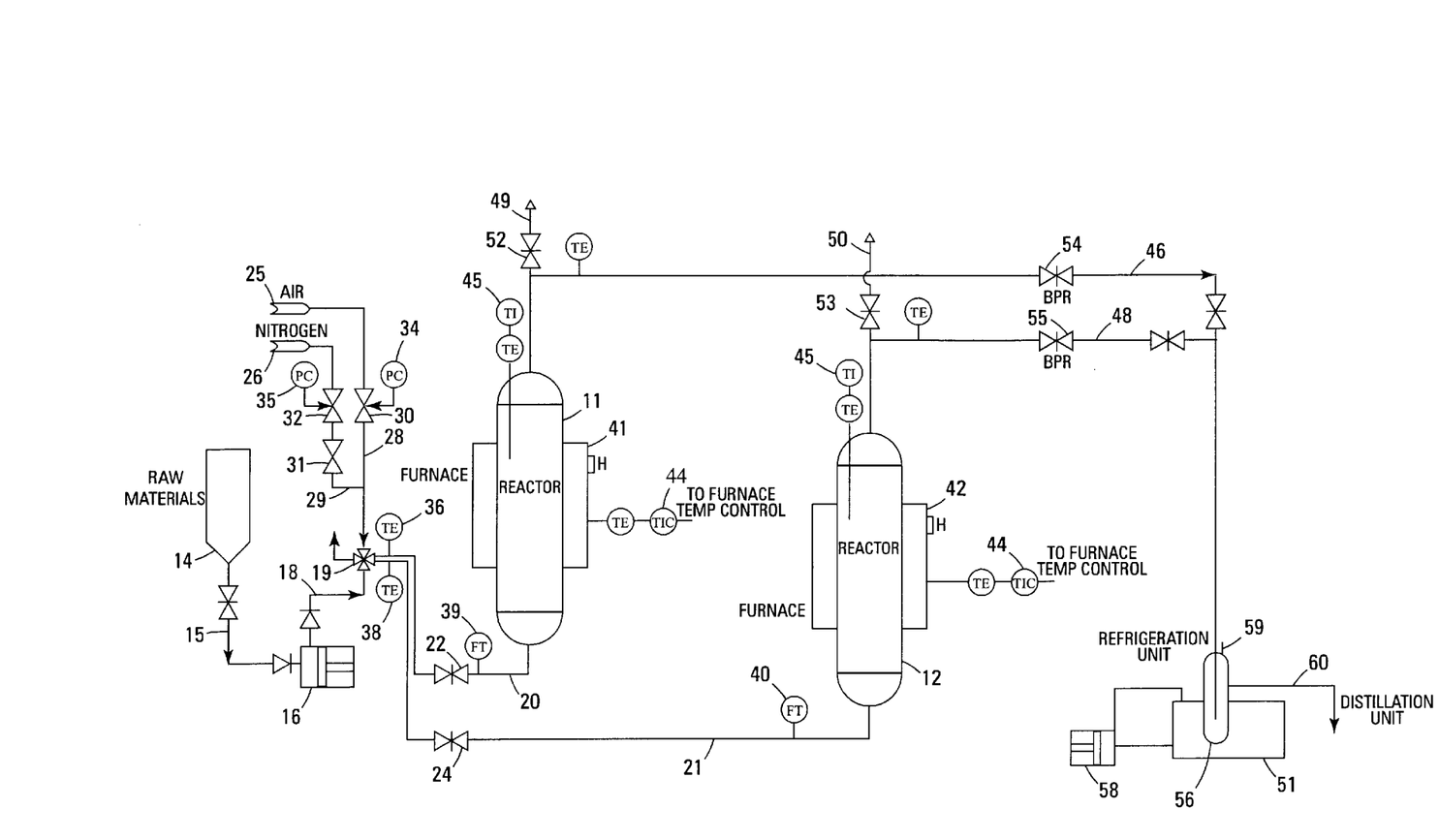
The single FIGURE is a schematic illustration of the method and apparatus involved in use of the catalyst structure of the present invention.

The method and system of using the catalyst structure in accordance with the present invention is understood best with reference to the drawing. In the drawing, the primary reaction members comprise a pair of vapor phase tube reactors 11 and 12. If desired or needed, more than two reactors could be provided to accommodate the specific reaction time or life cycle of the selected feed materials and the regeneration time of the selected catalyst. These reactors 11 and 12 are preferably conventional stainless steel catalytic tube reactors, which are filled with various combinations of an inert filler material, and a substantially theoretical monolayer catalyst as described above. In the preferred embodiment, the inert filler material is comprised of glass beads between about 3–10 mm in diameter, although it is contemplated that various other materials can be used as well such as stainless steel beads, lava rock and sand, among possible others. A portion of the reactors are also filled with a TML catalytic material in accordance with the present invention as described above to promote the desired reaction of the reactant materials.

The distribution of the catalyst structure within the reactors 11 and 12 can vary. Preferably, however, the bottom ⅓ of the reactor is filled with inert material in the form of glass beads, the middle third of the reactor is filled with catalyst and the top ⅓ of the reactor could be empty or filled with inert material in the form of glass beads.

In the preferred embodiment as shown, the reactors 11 and 12 are vertically oriented so that the feed materials pass vertically upwardly from the bottom to the top of the reactors. However, the benefits of the invention can also be realized with reactors having different orientations so that the feed materials flow downwardly or laterally through the reactors. These latter orientations are not as preferred, however, because of an increased tendency to plug.

The raw or reactive materials in accordance with the present invention are provided from a reactant material source or reservoir 14. In general, these reactant or feed materials will comprise a mixture of (1) a carboxylic acid or aldehyde or their derivatives and (2) a carboxylic acid. In the preferred embodiment, the reactant materials comprise a mixture of acetic acid and cyclopropylaldehyde or its derivatives (such as cyclopropanecarboxylic acid). The molar ratio of the acetic acid to the cyclopropanecarboxylic acid which makes up the feed stream or feed material is preferably in the range of 2:1 to 20:1. More preferably, the ratio of acetic acid to cyclopropanecarboxylic acid is about 3:1 to 8:1 and most preferably within a range of 3:1 to 5:1. The most preferred ratio is about 4:1.

If desired, the feed materials can be provided in separate reservoirs or from separate sources and then combined in the desired feed ratio. The feed material is fed from the reservoir 14 through a conduit 15 to a pump or pressure member 16 which discharges the feed material into the conduit 18 at an elevated pressure. The pressure is selected to optimize the reaction conditions (conversion and selectivity) and to maintain the feed materials in a gaseous state at the selected reaction temperature. In the preferred method and apparatus, the feed material is pressurized to a range of about 10 psig to about 200 psig, and more preferably to a pressure of about 20 psig to 100 psig. Most preferably, the pressure is provided at about 40 psig.

From the pump 16, the feed material is directed through the conduit 18 to a valve complex 19, which selectively directs the feed material either to the reactor feed conduit 20 or the reactor feed conduit 21. As shown, the feed conduits 20 and 21 are connected respectively, to the bottom ends of the reactors 11 and 12. The reactor feed conduits 20 and 21 include shutoff valves 22 and 24, respectively, for isolating the reactors 11 and 12 from the feed materials and facilitating the flow of purging or other materials, if desired. If more than two reactors are utilized, the valve complex 19 is modified and additional reactor feed conduits and shutoff valves are provided so that the flow of the feed materials can be selectively directed to each reactor, while selectively isolating one or more of the others.

The system of the present invention also includes a supply of purging and/or regeneration materials 25 and 26. Such materials may be provided from any available source such as a reservoir or the like. In the preferred embodiment, the materials 25 and 26 comprise air and nitrogen, respectively, although other materials known in the art can be used as well such as hydrogen and methane. The materials are used during purging or preheating of the reactors 11 or 12 or during regeneration of the catalyst within the reactors 11 and 12. The materials 25 and 26 are provided to the valve 19 through the conduits 28 and 29, respectively. The conduits 28 and 29 are also provided with a plurality of shutoff valves 30, 31 and 32 to selectively control the flow of materials 25 and 26 to the valve 19. Pressure regulators 34 and 35 are associated with the valves 30 and 32. The valve 19 functions to selectively direct the flow of materials 25 and/or 26 to either the reactor feed conduit 20 or the reactor feed conduit 21. The conduits 20 and 21 are provided with temperature gauges 36 and 38, respectively, upstream of the valves 22 and 24.

The reactors 11 and 12 are also provided with heating means 41 and 42 and means in the form of temperature control and regulators 44 for selectively controlling the heaters 41 and 42. Means for monitoring the temperature and pressure within the reactor are also provided on each reactor 11 and 12 in the form of the pressure and temperature monitors 45.

Outflow or product exit conduits 46 and 48 are connected with the top or upper ends of the reactors 11 and 12, respectively, for directing the outflow from the reactors to a product separation means 51. Connected with each of the conduits 46 and 48 is a secondary or waste conduit 49 and 50, respectively, for purging or regeneration material, which is not desired to be, directed to the recovery means 51. Appropriate valves 52, 53, 54 and 55 are provided in the conduits 49, 50, 46 and 48, respectively, for controlling the flow of the product and waste streams. If more than two reactors are provided, additional exit conduits, waste conduits and associated valves are also provided.

The product recovery means 51 includes a receiver, a precipitation or distillation column 56 and a pressure means or pump 58 to recover the preferred product, namely, methyl cyclopropyl ketone (MCPK) from the exit stream. In FIG. 1, the MCPK is recovered through the conduit 60, with the other materials or co-products being recovered through the conduit 59.

Having described the apparatus and system of the present invention in detail, the method of using the catalyst structure may be understood best as follows. First, one of the reactors 11 and 12 is selected for initial use in the process of the present invention. For purposes of describing the preferred method of the present invention, the reactor 11 will be selected. In such case, the other reactor 12 is isolated from the system by closing the valves 24, 53 and 55. The reactor 11 is then prepared for preparation of the ketone, specifically MCPK, by activating the heater 41 and providing a purging gas from the sources 25 and/or 26, through the valve 19 and into the lower end of the reactor 11. In accordance with the preferred method, the reactor 11 is preheated by the heater 41 to a temperature in the range of 350° C. to 500° C. and more preferably in the range of 400° C. to 440° C. Most preferably, in accordance with the present invention, the optimum reaction temperature is first determined and the reactor is heated to this temperature. This optimum temperature will vary to some extent with the composition of the feed stream, the concentration and type of catalyst, the liquid or weight hourly space velocity at which the reactor will be run, etc. The reactor 11 is then heated to this optimum temperature.

When the optimum temperature is reached, the valve 19 is actuated to stop the flow of the purging or other gas to the reactor 11 and to provide feed material of the desired composition from the reservoir or source 14. In the preferred embodiment, this feed material is a mixture of acetic acid arid cyclopropanecarboxylic acid in the ratios set forth above. This pressurized feed stream is supplied to the bottom of the reactor 11 so that the vaporized feed materials enter the reactor from the bottom and flow upwardly through the glass beads, the TML catalyst structure and the glass beads before exiting through the top of the reactor 11. During this process, the material in the feed stream and the conduit 20 is sufficiently pressurized by the pressure means 16 to maintain the feed materials in a gaseous state at the reaction temperature. The feed materials are fed through the reactor at a rate sufficient to provide a liquid or weight hourly space velocity in excess of 1, more preferably in excess of 2 and most preferably in the range of 5–20 or 10–20. As used herein and as known in the art, weight (or liquid) hourly space velocity (WHSV or LHSV) is the amount of raw material (unit weight or volume) per unit weight or volume of catalyst per hour.

Within the reactor 11, the feed material reacts in the presence of the TML catalyst and at the optimum temperature, to produce MCPK or other desired ketone along with other byproducts or co-products including acetone, and dicyclopropyl ketone. When the valve 52 is closed and the valve 54 open, this exit or product stream is then directed via the conduit 46 to the recovery means 51 where the MCPK and other co-products are separated from one another. Preferably, this separation/recovery process is a precipitation or distillation process known in the art.

With the method and apparatus as described above, conversion rates in excess of 80% can be achieved with conversion rates commonly in the range of 95%–99%. Also, with the above method and apparatus, selectivity of the converted feed stream to MCPK in excess of 50% and commonly in the range of 70%–85% can be achieved.

In the event the reactor 11 requires maintenance or for some reason the reactor becomes plugged or the catalyst needs regeneration, the second reactor 12 can be quickly and easily utilized without resulting in downtime and thus loss of production or production rate. To accomplish this conversion to the reactor 12, the reactor 12 can be brought up to the optimum temperature and the valve 24 can be opened to allow the flow of purging or other gas into the bottom of the reactor 12 through the reactor and out through the conduit 50. Once the optimum temperature has been reached and the reactor 12 has been sufficiently purged, the valve 19 is adjusted to direct the feed material from the reservoir 14 into and through the conduit 21 and through the reactor 12. When this is done, the valves 53 and 54 are closed and the valve 55 is opened. The previously used reactor 11 is then isolated from the feed materials and can be isolated entirely from the system by closing the valve 22 or can be provided with purging or regeneration material from the sources 25 and 26 if desired.

In the above-described MCPK process, the reaction time or reaction life cycle is greater than the catalyst regeneration time. Thus, a pair of reactors 11 and 12 is sufficient to provide a continuous ketone production process. As used herein, the term "reaction time" or "reaction life cycle" is the time during which acceptable reaction conditions exist (i.e., before catalyst regeneration is needed or plugging occurs) for the selected feed materials and selected catalyst at the specific reaction variables of temperature, pressure, WHSV and the like. The term "regeneration time" is the time needed to regenerate the selected catalyst. If the specific feed materials, catalyst and reaction variables are such that the reaction time or life cycle is less than the regeneration time. More than two reactors are needed to maintain a continuous ketone production process.

Although the description of the preferred embodiment and method have been quite specific, it is contemplated that various modifications could be made without deviating from the spirit of the present invention. Accordingly, it is intended that the scope of the present invention be dictated by the appended claims rather than by the description of the preferred embodiment.

I claim:

1. A method of preparing a ketone comprising the steps of:
providing a raw material feed of first and second materials, which react in a ketone production reaction to produce said ketone;
providing a catalytic bed of a catalyst structure comprised of a catalyst support with an available surface area for a catalyst of greater than 20 $m^2$ per gram of said catalyst support and a catalyst suitable for said ketone production reaction in an amount at or near a theoretical monolayer, but not greater or less than 10% of a theoretical monolayer;
passing said first and second feed materials through said catalytic bed at a temperature of 350 to 500° C. and at a weight hourly space velocity (WHSV) of greater than 5; and
separating said ketone.

2. The method of claim 1 wherein said ketone is methyl cylopropyl ketone.

3. The method of claim 2 wherein said first and second feed materials are cyclopropanecarboxylic acid and acetic acid, respectively.

4. The method of claim 3 wherein said catalyst support is one or a combination of the following: aluminum oxide ($Al_2O_3$), zinc oxide (ZnO), zirconium oxide ($ZrO_2$), and titanium oxide ($TiO_2$), and where said catalyst is one or a combination of the following: zinc oxide (ZnO), cerium oxide ($CeO_2$ or $Ce_2O_3$), other lanthanide metals and metal oxides, and group IIIB, IVB, and VB metals and metal oxides.

5. The method of claim 4 said catalyst support is one or a combination of aluminum oxide ($Al_2O_3$), zirconia oxide (ZrO2) and said catalyst is one or a combination of cerium oxide ($CeO_2$ or $CeO_3$) and zinc oxide (ZnO).

* * * * *